(12) United States Patent
Chen

(10) Patent No.: US 6,432,082 B1
(45) Date of Patent: Aug. 13, 2002

(54) SAFETY SYRINGE

(76) Inventor: Cho-Ying Chen, No. 93, Tachou Rd., Tashe Tsun, Shenkang Hsiang, Taichung County (TW)

( * ) Notice: Subject to any disclaimer, the term of this patent is extended or adjusted under 35 U.S.C. 154(b) by 0 days.

(21) Appl. No.: 09/811,476

(22) Filed: Mar. 20, 2001

(51) Int. Cl.[7] ............................................. A61M 5/32
(52) U.S. Cl. ................ 604/110; 604/181; 604/187; 604/218; 604/240; 604/243
(58) Field of Search .......................... 604/110, 181, 604/187, 198, 197, 192, 218, 228, 263, 240, 243

(56) References Cited

U.S. PATENT DOCUMENTS

| | | | | |
|---|---|---|---|---|
| 5,000,738 A | * | 3/1991 | LaVallo et al. | 604/110 |
| 5,053,018 A | * | 10/1991 | Talonn et al. | 604/198 |
| 5,180,370 A | * | 1/1993 | Gillespie | 604/110 |
| 5,205,824 A | * | 4/1993 | Mazur | 604/110 |
| 5,401,246 A | * | 3/1995 | Mazur et al. | 604/110 |
| 5,403,287 A | * | 4/1995 | Talonn et al. | 604/198 |
| 5,980,487 A | * | 11/1999 | Jones et al. | 604/110 |
| 5,997,511 A | * | 12/1999 | Curie et al. | 604/110 |

* cited by examiner

*Primary Examiner*—James Hook
(74) *Attorney, Agent, or Firm*—Rosenberg, Klein & Lee

(57) ABSTRACT

A safety syringe in which the needle holder has a mounting unit fixedly fastened to the front end of the barrel, a body holding a needle cannula outside the barrel, a breakable slotted connecting portion connected between the mounting unit and the body, and a rear engagement block, and the plunger has a front tubular retaining member adapted to engage the rear engagement block for enabling the needle cannula with the body of the needle holder to be separated from the mounting unit and moved backwards with the plunger to the inside of the barrel after the service of the safety syringe.

2 Claims, 4 Drawing Sheets

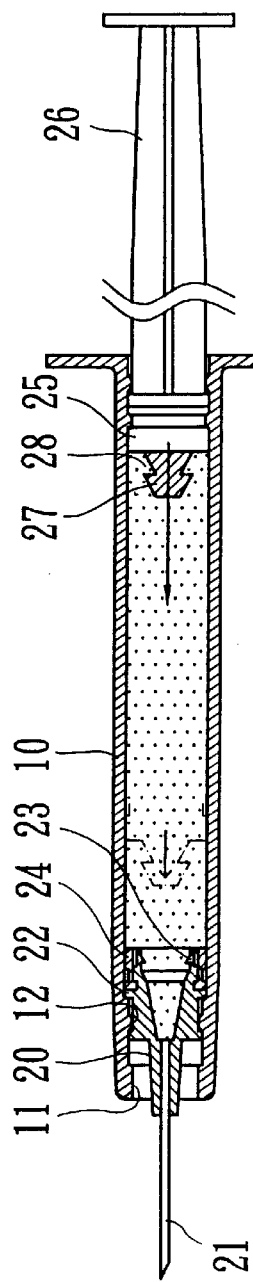
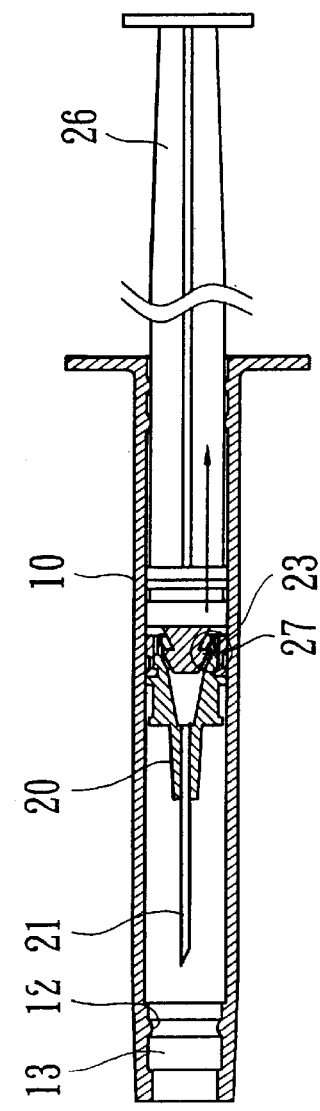
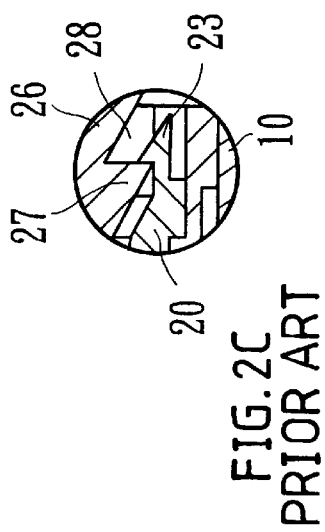
FIG.2A PRIOR ART
FIG.2B PRIOR ART
FIG.2C PRIOR ART

SAFETY SYRINGE

BACKGROUND OF THE INVENTION

The present invention relates to syringe and, more specifically, to a safety syringe, which keeps the needle holder against vibration and prevents disconnection of the needle holder from the barrel during normal use and, enables the needle cannula with the body of the needle holder to be moved backwards with the plunger and received inside the barrel after the service of the safety syringe.

FIGS. 1 and 2 show a safety syringe according to the prior art. This structure of safety syringe comprises a barrel 10, a needle holder 20 holding a needle cannula 21, and a plunger 26. The barrel comprises a plurality of inside annular flanges 11 and 12 disposed around the inside wall of the front end thereof and defining two parallel inside annular grooves 13. The needle holder comprises a peripheral positioning flange 22 and two symmetrical rear hooks 23, and is mounted with a seal ring 24. The peripheral positioning flange 23 and the seal ring 24 are respectively engaged into the inside annular grooves 13 of the barrel 10, keeping the needle holder 20 secured to the front end of the barrel 10. The plunger 26 has a front end peripherally mounted with seal ring 25, and a front engagement block 27 forwardly axially extended from the front end. The front engagement block 27 has a peripheral groove 28. Before the use the safety syringe, the engagement block 27 does not touch the needle holder 20 (see FIG. 2A). After the service of the safety syringe, the engagement block 27 is forced into engagement with the rear hooks 23 of the needle holder 20, and then the plunger 26 is pulled backwards to carry the needle holder 20 and the needle cannula 21 backwards to the inside of the barrel 10. This structure of safety syringe is still not satisfactory in function. The drawbacks of this structure of safety syringe are numerous and outlined hereinafter.

1. The positioning of the needle holder 20 in the front end of the barrel is achieved by means of engaging the peripheral positioning flange 22 into one inside annular groove 13 of the barrel 10. Due to tooling technical problem. the protruding distance of the peripheral positioning flange 22 from the peripheral wall of the needle holder 20 is limited. In case an excessive forward pressure is imparted to the needle holder 20 during injection, the needle holder 20 will be forced out of the barrel 10.
2. Because the needle holder 20 has only two rear hooks 23 hooked on the engagement block 27 at two sides, the engagement between the engagement block 27 and the needle holder 20 is unstable. and the plunger 26 may slip from the needle holder 20 when pulled backwards.
3. Because the resisting force between the barrel 10 and the needle holder 20 is strong at the initial stage when pulling the plunger 26 backwards to carry the needle holder 20 back to the inside of the barrel 10, a rod-like tool or the like may be needed to push the needle holder 20 backwards. When forcing the needle holder 20 backwards with a tool or the like, the fingers may be injured by the needle cannula 21 accidentally.
4. When moving the plunger 26 forwards to squeeze medicine out of the barrel 10 through the needle cannula 21 into the patient's body, the engagement block 27 is automatically forced into engagement with the rear hooks 23 of the needle holder 20, thus the safety syringe cannot be used again. In case the patient has to take two injections, a new safety syringe must be used.

SUMMARY OF THE INVENTION

The present invention has been accomplished to provide a safety syringe, which eliminates the aforesaid drawbacks. It is one object of the present invention to provide a safety syringe, which prevents vibration of the needle holder during the application of the safety syringe. It is another object of the present invention to provide a safety syringe, which enables the needle cannula with the body of the needle holder to be easily separated from the mounting unit of the needle holder so that the needle cannula and the body of the needle holder can be moved backwards with the plunger and received inside the barrel after the service of the safety syringe. According to one aspect of the present invention, the needle holder of the safety syringe has a mounting unit fixedly fastened to the front end of the barrel, a body holding a needle cannula outside the barrel, a breakable slotted connecting portion connected between the mounting unit and the body, and a rear engagement block. The plunger of the safety syringe has a front tubular retaining member adapted to engage the rear engagement block for enabling the needle cannula with the body of the needle holder to be separated from the mounting unit and moved backwards with the plunger to the inside of the barrel after the service of the safety syringe. According to another aspect of the present invention, the tubular retaining member of the plunger comprises a radially expansible front lip shaped like a tapered cylinder, the front lip having a thin bottom connecting portion connected to the retaining member. The front lip stops the tubular retaining member from engaging the rear engagement block of the needle holder unless the user gives a high forward pressure to the plunger against the rear engagement block of the needle holder. Thus, the safety syringe can be used twice for the same patient.

BRIEF DESCRIPTION OF THE DRAWINGS

FIG. 2A is a sectional view of the prior art safety syringe.

FIG. 2B illustrates the needle cannula and the needle holder pulled backwards with the plunger and received inside the barrel according to the prior art.

FIG. 2C illustrates the connection between the plunger and needle cannula in the prior art syringe of FIGS. 2A and 3.

DETAILED DESCRIPTION OF THE PREFERRED EMBODIMENT

Figure 1A:
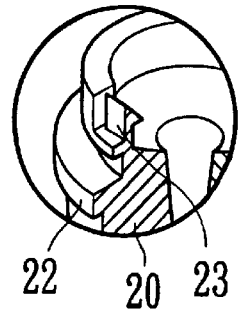
FIG. 1A is an enlarged view of a part of FIG. 1.
Figure 1:
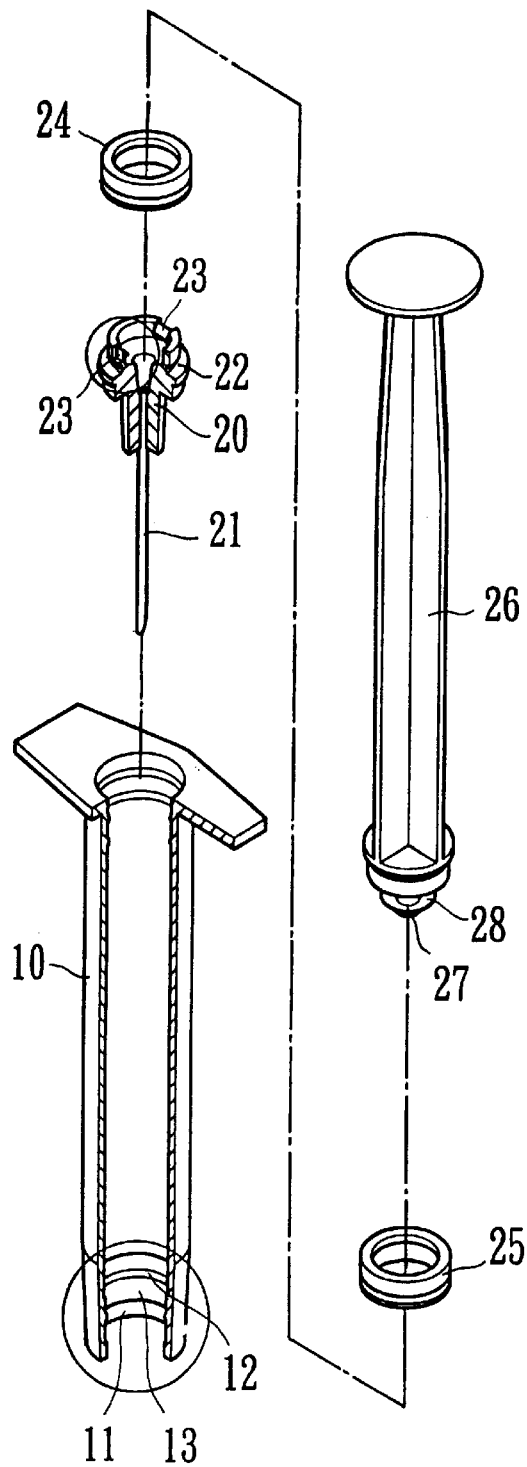
FIG. 1 is an exploded cutaway view of a safety syringe according to the prior art.
Figure 1B:
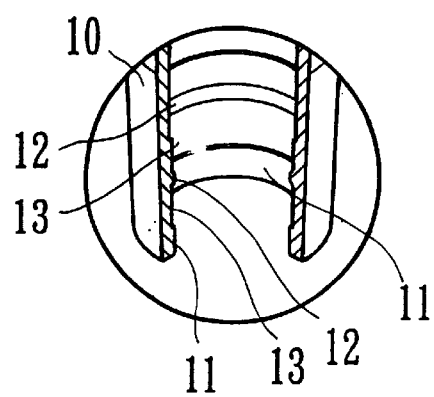
FIG. 1B is an enlarged view of another part of FIG. 1.
Figures 3, 3A, 3B:
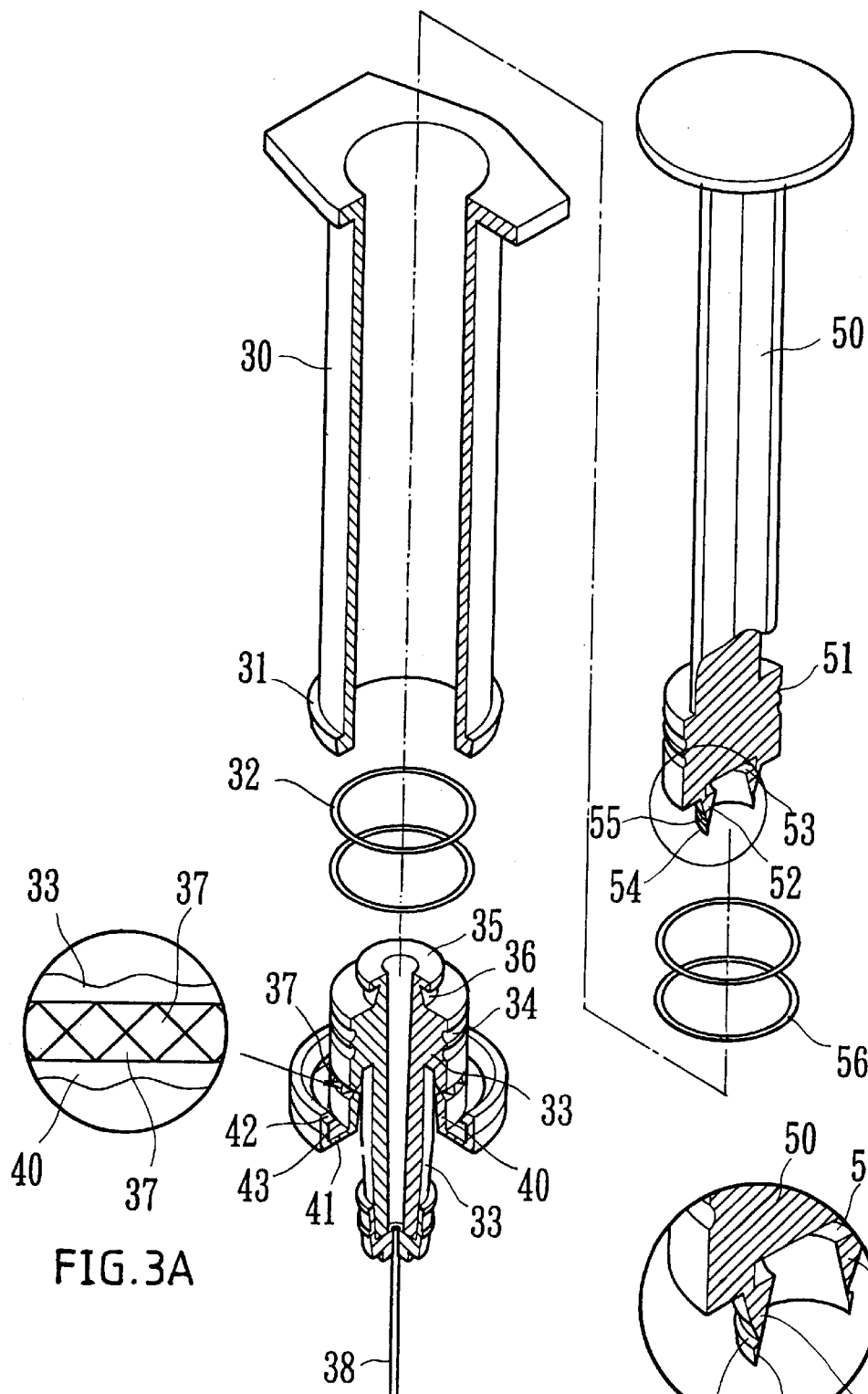
FIG. 3 is an exploded, cutaway view of a safety syringe constructed according to the present invention.
FIG. 3A is an enlarged view of a part of the mounting unit of the needle holder of the safety syringe shown in FIG. 3.
FIG. 3B is an enlarged view of the front end of the plunger of the safety syringe shown in FIG. 3.

Referring to FIGS. 3 and 4, a safety syringe in accordance with the present invention is generally comprised of a barrel 30, a needle holder 33 holding a needle cannula 38, and a plunger 50. The needle holder 33 is mounted in one end of the barrel 30 to hold the needle cannula 38 outside the barrel 30, comprising a plurality of annular grooves 34 disposed around the periphery, and a plurality of seal rings 32 respectively mounted in the annular grooves 34 and stopped against the inside wall of the barrel 30 to seal the gap. The plunger 50 is slidably inserted into the barrel 30, comprising a plurality of annular grooves 51 around the periphery of the front end thereof, and a plurality of seal rings 56 respectively mounted in the annular grooves 51 and stopped against the inside wall of the barrel 30 to seal the gap. When pulling the plunger 50 backwards after the service of the safety syringe (after forward stroke of the plunger 50 to squeeze the medicine or liquid out of the barrel 30), the needle holder 33 is moved with the plunger 50, enabling the needle cannula 38 to be received with the needle holder 33 inside the barrel 30.

Referring to FIGS. 3 and 4 again, the barrel 30 comprises a coupling flange 31 around the periphery of the front end thereof. The needle holder 33 comprises a mounting unit 40 fastened to the front end of the barrel 30, a slotted narrow connecting segment 37 peripherally connecting the mounting unit 40 to the body of the needle holder 33, a rear engagement block 35 axially extended from the rear end thereof, and a retaining groove 36 around the periphery of the rear engagement block 35. The mounting unit 40 comprises an angled peripheral coupling flange 41, and a hooked portion 42 protruded from the free end of the peripheral coupling flange 41 and defining with the angled peripheral coupling flange 41 a coupling groove 43. The angled peripheral coupling flange 41 is covered over the front end of the barrel 30 to force the hooked portion 42 to hook on the coupling flange 31 of the barrel 30, keeping the coupling flange 31 engaged into the coupling groove 43. The plunger 50 comprises a tubular retaining member 52 axially forwardly extended from the front end thereof and adapted to engage the rear engagement block 35 of the needle holder 33. The tubular retaining member 52 defines an engagement chamber 53 adapted to receive the rear engagement block 35 of the needle holder 33, and has a elastic front lip 54 shaped like a tapered cylinder. The front lip 54 has a thin bottom connecting portion 55 connected to the retaining member 52. Normally, the front lip 54 stops the tubular retaining member 52 from engaging the rear engagement block 35 of the needle holder 33. However, when the user pushes the plunger 50 forwards with force after the service of the safety syringe, the front lip 54 is forced to expand radially outwards, enabling the tubular retaining member 52 to be forced into engagement the rear engagement block 35 of the needle holder 33.

Figure 4A:
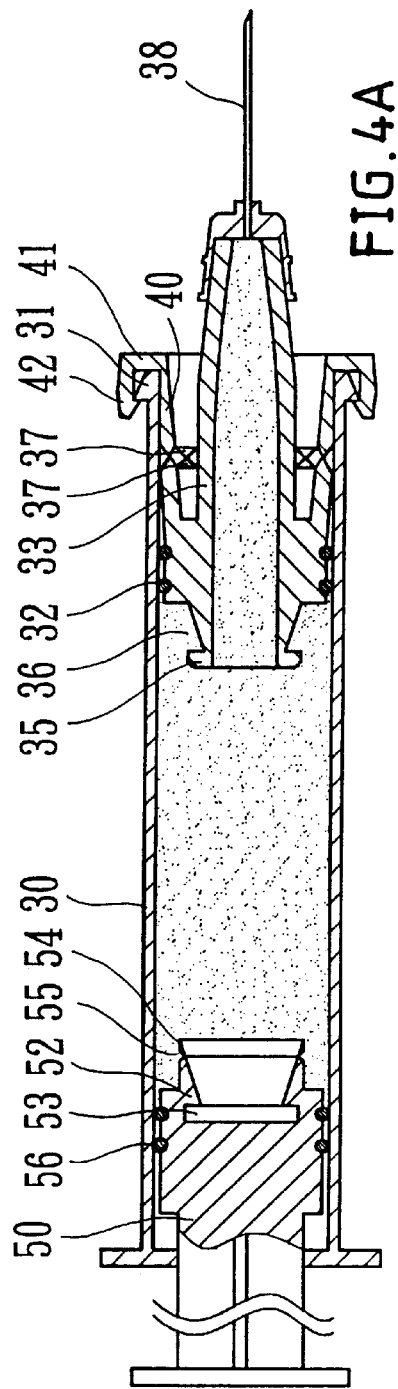
FIG. 4A is a sectional view of the safety syringe according to the present invention.

Referring to FIG. 4A, the coupling groove 43 of the mounting unit 40 of the needle holder 33 is forced into engagement with the coupling flange 31 of the barrel 30, keeping the needle holder 33 and the barrel 30 firmly secured together, and the seal rings 32 seal the gap between the needle holder 33 and the barrel 30. Because the hooked portion 42 of the mounting unit 40 is hooked on the coupling flange 31 of the barrel 30 to hold the coupling flange 31 in engagement with the coupling groove 43, the needle holder 33 is prohibited from vibration relative to the barrel 30, and therefore applied medicine or liquid can be smoothly squeezed out of the barrel 30 through the needle cannula 38 into the patient's body.

Figure 4B:
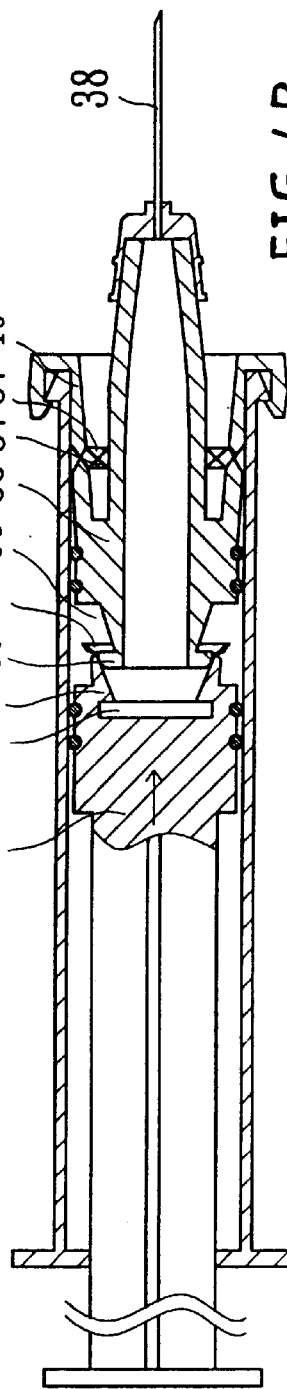
FIG. 4B is another sectional view of the present invention showing the tubular engagement member of the plunger forced into engagement with the rear engagement block of the needle holder according to the present invention.
Figure 4C:
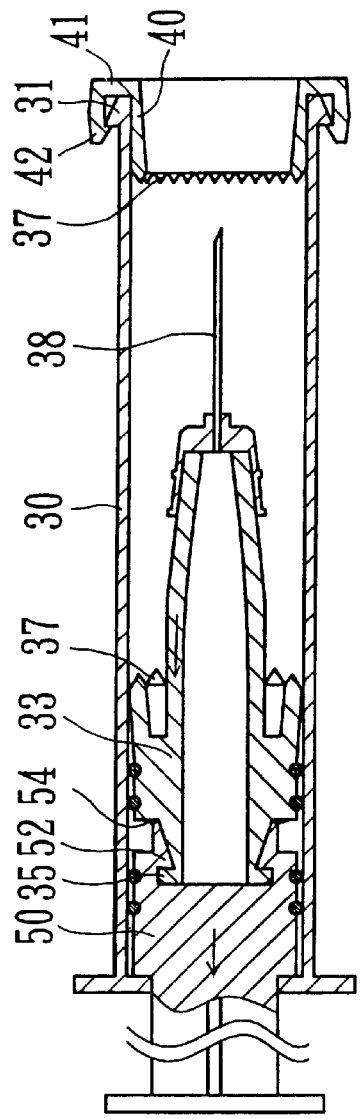
FIG. 4C is still another sectional view of the present invention showing the plunger pulled backwards, the needle cannula and the body of the needle holder received inside the barrel.

Referring to FIGS. 4B and 4C, after the service of the safety syringe, the plunger 50 is forced forwards with force. At this time, the front lip 54 of the tubular retaining member 52 is forced to expand radially outwards, enabling the tubular retaining member 52 to be forced into engagement the rear engagement block 35 of the needle holder 33. After engagement of the tubular retaining member 52 with the rear engagement block 35 of the needle holder 33, the plunger 50 is pulled backwards. When pulling the plunger 50 backwards with force after engagement of the tubular retaining member 52 with the rear engagement block 35 of the needle holder 33, the slotted narrow connecting segment 37 breaks, and therefore the needle holder 33 is separated from the mounting unit 40 and moved backwards with the plunger 50. enabling the needle cannula 38 to be received with the needle holder 33 inside the barrel 30.

A prototype of safety syringe has been constructed with the features of the annexed drawings. The safety syringe functions smoothly to provide all of the features discussed earlier.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. A safety syringe comprising a barrel having a front end and a rear end, a needle holder fastened to the front end of said barrel and holding a needle cannula in front of said barrel, and a plunger inserted through the rear end of said barrel into the inside of said barrel and adapted to squeeze a medicine out of said barrel through said needle cannula and to pull said needle holder and said needle cannula backwards to the inside of said barrel after the service of the safety syringe, wherein:

said barrel comprises a coupling flange around the periphery of the front end thereof;

said needle holder comprises a mounting unit mounted on the front end of said barrel and fastened to the coupling flange of said barrel, a slotted narrow connecting segment peripherally connecting said mounting unit to a body thereof, a rear engagement block axially backwardly extended from said body, and a retaining groove around the periphery of said rear engagement block, said mounting unit comprising an angled peripheral coupling flange, and a hooked portion protruded from said angled peripheral coupling flange and defining with said angled peripheral coupling flange a coupling groove, said angled peripheral coupling flange being covered over the front end of said barrel, said hooked portion being hooked on the coupling flange of said barrel;

said plunger comprises a tubular retaining member axially forwardly extended from a front end thereof and adapted to engage the rear engagement block of said needle holder for enabling the said needle cannula with the body of said needle holder to be separated from said mounting unit and moved backwards with said plunger when pulling said plunger backwards after engagement of said tubular retaining member with the rear engagement block of said needle holder, said tubular retaining member defining an engagement chamber adapted to receive the rear engagement block of said needle holder.

2. The safety syringe of claim 1 wherein said tubular retaining member comprises a radially expansible front lip shaped like a tapered cylinder, said front lip having a thin bottom connecting portion connected to said retaining member.

* * * * *